United States Patent [19]

Howell et al.

[11] Patent Number: 5,252,342

[45] Date of Patent: Oct. 12, 1993

[54] ENHANCEMENT OF ANTI-NEOPLASTIC DRUG EFFICACY USING EGF

[75] Inventors: Stephen B. Howell, Del Mar; Randloph D. Christen, San Diego; Seiji Isonishi, San Diego; Paul A. Andrews, San Diego, all of Calif.

[73] Assignee: The Regents of the University of California, Oakland, Calif.

[21] Appl. No.: 488,199

[22] Filed: Mar. 5, 1990

[51] Int. Cl.$^5$ ................ A61K 33/24; A61K 31/00
[52] U.S. Cl. ........................ 424/649; 514/2; 514/19
[58] Field of Search ............ 514/2, 12, 14, 19, 546, 514/649; 424/643, 649, 10

[56] References Cited

U.S. PATENT DOCUMENTS

| | | | |
|---|---|---|---|
| 4,571,336 | 2/1986 | Houck et al. | 514/21 |
| 4,863,902 | 9/1989 | Harunbu et al. | 514/12 |
| 4,925,922 | 5/1980 | Byers et al. | 530/391 |
| 4,959,353 | 9/1990 | Brown et al. | 514/12 |
| 4,962,091 | 10/1990 | Eppstein et al. | 514/2 |

OTHER PUBLICATIONS

C.A. vol. 106 (21)-169447(u).
C.A. vol. 109 (25)-222460(h).
C.A. vol. 110 (9)-69068(k).
C.A. vol. 113 (21)-185362(n).

*Primary Examiner*—Jerome D. Goldberg
*Assistant Examiner*—T. J. Criares
*Attorney, Agent, or Firm*—Walter H. Dreger

[57] ABSTRACT

The present invention comprises a method of sensitizing cancer cells to cisplatin or other cytotoxic agents and augmenting the sensitivity of cancer cells to these cytotoxic agents. The invention provides a method to treat cancer and other cell proliferative diseases by the administration of a sensitizing agent prior to or concurrently with the administration of a cytotoxic agent.

1 Claim, 9 Drawing Sheets

ENHANCEMENT OF ANTI-NEOPLASTIC DRUG EFFICACY USING EGF

FIELD OF THE INVENTION

This invention relates to cancer treatment and to augmentation of anti-neoplastic drug efficacy.

BACKGROUND OF THE INVENTION

Cisplatin (DDP) is one of the most widely used antineoplastic agents for the treatment of human ovarian cancer (Ozois and Young, *Semin. Oncol.* 11: 251-263 (1984); Hakes, et al., *Proc. Am. Sci. Clin. Oncol.* 8: 152 (1989)). In spite of its potency, the frequent development of DDP resistance is a major obstacle to curative therapy (Chu, et al., *Proc. Am. Assoc. Cancer Res.* 30: 594 (1989); Meitner, et al., *Proc. Am. Assoc., Cancer Res.* 30: 508 (1989)). Although the mechanism of DDP resistance in vivo is not characterized, a good deal of information is available about mechanisms in cell lines Impairment of DDP uptake is one of the important mechanisms contributing to DDP resistance (Andrews, et al., *Cancer Res.* 48: 68-73 (1988); Waud, *Cancer Res.* 47: 6549-655 (1987); Richon, et al., *Cancer Res.* 47: 2056-2061 (1987); Teicher, et al., *Cancer Res.* 47: 388-393 (1987)). Increased levels of metallothioneins have also been reported in some (Kelley, et al., *Science* 241, 1813-1815 (1988)), but not all (Andrews, et al., *Cancer Chemother Pharmacol.* 19: 149-154 (1987)), DDP-resistant cells. Kelley et al. reported that, in a murine leukemia cell line, the degree of resistance was proportional to metallothionein content, and that loss of resistance to DDP in a revertant cell line was associated with concomitant lowering of metallothionein content. Modulation of glutathione (GSH) concentrations in mammalian cells has also been reported to influence the cytotoxicity in DDP (Lee, et al., *Cancer Res.* 48: 3661-3665 (1988)). Some DDP-resistant cell lines contain increased amounts of glutathione (Rice, et al., *Cancer Res.* 46: 6105-6110 (1986)), and DDP sensitivity can be enhanced under some conditions by extensive depletion of *Mot. Pharmacol.* 30: 643-650 (1986)). DDP reacts with DNA to produce an intrastrand N7d(GpG) diamine platinum adduct which comprises 40-60% of the platinum bound to DNA (Poivier, et al., *Proc. Natl. Acad. Sci. U.S.A.* 79: 6443-6447 (1982)). DNA repair defective cells are hypersensitive to DDP (Fox and Roberts, *Cancer Metastisis Rev.* 6: 261-281 (1987)), and enhanced DNA repair has been implicated in the DDP-resistant phenotype (Masuda, et al., *Cancer Res.* 48: 5713-5716 (1988)).

The tumor-promoting phorbol diester TPA (12-0 tetradecanoyl phorbol-3-acetate) has profound effects on a variety of cellular functions depending upon the type of cell treated, including either stimulation (Diamond, et al., *Int. J. Cancer* 13: 721-730 (1974); Dridger and Blumberg *Cancer Res.* 37: 3257-3265 (1977)), inhibition (Diamond, et al., *Nature* 269: 247-249 (1977); Cohen, et al., *Nature* 266: 538-540 (1977)) of proliferation, or induction of differentiation (Dridger and Blumberg *Cancer Res.* 37: 3257-3265 (1977); Diamond, et al., *Nature* 269: 247-249 (1977)). The effects of TPA appear to be largely mediated through stimulation of protein kinase C and the subsequent phosphorylation of a variety of protein substrates (Blacksher, et al., *FASEB* 2: 2957-2969 (1988); Nishizuka, *Nature* 308: 693-698 (1988)).

TPA has been reported to alter cellular sensitivity to several kinds of antineoplastic agents. In the human KB carcinoma cells, TPA treatment decreased sensitivity to etoposide and vincristine by 50%, but this effect could not be mimicked by treatment of cells with 1-oleoyl-2-acetylglycerol (OAG), calling into question a 47; 433-441 (1987)). Posada (Posada, et al., *J. Biol. Chem.*, in press (1990)) demonstrated that TPA enhanced the cytotoxic activity of doxorubicin in sarcoma 180 cells. Conversely, down regulation of protein kinase C produced by long term exposure to TPA resulted in a decreased cytotoxic effect of doxorubicin (Posada et al., *J. Biol. Chem.*, in press (1990)). Protein kinase C can phosphcrylate the MDR 1 gene product, which functions as efflux pump for etoposide, vincristine, and doxorubicin. Hofmann (Hofmann, et al., *Int. J. Cancer* 42: 382-388 (1988)) reported that either inhibition of protein kinase C activity with a series of compoundation such as quercetin (3,3', 4'5,7 pentahydroxyflavone), tamoxifen, staurosporine, either lipid analog (BM41440 (26Hofmann, et al., *Lipids* 24: 312 317 (1989)), or down regulation with long term exposure to TPA enhanced the sensitivity of cells to DDP.

Platinum complexes, particularly cisplatin (DDP), are drugs of major importance in cancer therapy. However, both intrinsic and acquired resistance to DDP occurs frequently. Cells selected for resistance to many antimetabolites (Kaufman, et al., *Proc. Natl. Acad. Sci. U.S.A.* 76: 5669 (1979)), and to drugs participating in the multiple drug resistance phenotype (Gottesman and Pastan, *J. Biol. Chem.* 263: 12163 (1988)), often exhibit very high levels of resistance. In contrast, both in vitro and in vivo selection with DDP at clinically relevant intensities usually results in cells only 2 to 4 fold resistant to this drug (Wilson, et al., *Br. J. Cancer* 56: 763 (1987)). Attempts to enhance the sensitivity to DDP have focused on strategies such as reduction of glutathione (Andrews, et al., *Chem. Bi Interactions* 65: 51 (1988)) and inhibition of DNA repair (Hamilton, et al., *Proc. A. Assoc. Cancer Res.* 28: 291 (1987)).

SUMMARY OF THE INVENTION

The present invention discloses a method of sensitizing cancer cell to cisplatin or other cytotoxic agents and augmenting the sensitivity of cancer cells to these cytotoxic agents. The present invention comprises administering a sensitizing agent selected from the group consisting of Epidermal Growth Factor (EGF), TPA, retinoic acid, estrogen, progesterone, triiodothyronine, androgens and analogs thereof to an individual in need of such treatment.

The term "analog" means any structurally related compound which mimicks the biological activity of a sensitizing agent. Of particular interest as analogs are the steroid like analogs of estrogen, progesterone, and the androgens.

The sensitizing agent is preferably administered in advance of or conconcurrently with the cytotoxic agent. In one embodiment, the sensitizing agent is administered following the administration of the cytotoxic agent. The sensitizing agent is administered in an amount which causes an increased sensitivity of the cancer cells to the cytotoxic agent and thus, enhances the efficacy of the cytotoxic agent.

In another embodiment the sensitizing agent additionally increases the selectively of the cytotoxic drug. For instance, one skilled in the art will recognize that the modulators of cisplatin sensitivity will increase the toxicity of cisplatin by enhancing the effectiveness of cisplatin on cells which have receptors for the sensitizing agent. As is discussed herein, many malignant cells have a greater number of EGF receptors than normal cells. Therefore, not only will the cytotoxic effect of cisplatin be enhanced, but it will be selectively augmented in cells containing higher receptor numbers. The term "selectively" as used in this context means the ability of the sensitizer or modulator to increase the toxicity of the cytotoxic drug to a greater extent in abnormally proliferating cells than in normal cells.

In a preferred embodiment, the cytotoxic agent is cisplatin. However, other cytotoxic agents may also be utilized to practice the present invention. In one embodiment, one skilled in the art can readily determine the effective dosage of the sensitizing agent by reference to the amount of TPA utilized in vitro which increases the sensitivity in cultured human ovarian carcinoma cells to DDP. Since TPA produces this effect via protein kinase C, one will readily ascertain that other agents which act through the protein kinase C pathway will also be useful in practicing the present invention. The inventors have demonstrated that this sensitizing effect occurs in the absence of a change in cellular accumulation of DDP and thus implicates a phosphoprotein as major determinant of the activity of DDP once it has entered the cell. In addition, one of skill in the art will readily recognize that since the naturally occuring signal transduction pathway, mediated by epidermal growth factor (EGF), can both enhance sensitivity to DDP, and produce morphologic changes consistent with activation of a differentiation program in two human ovarian carcinoma cell lines, other agents which mimic this effect of EGF will also be useful in practicing this invention.

In another embodiment, the sensitizing agent is also useful to modulate the repair of DNA adducts or lesions caused by the cytotoxic agents. For instance, when a sensitizing agent such as EGF is administered after the administration of the cytotoxic agent cisplatin, the normal cellular mechanism for repairing DNA are diminished. Therefore, in cells damaged by, for instance, cisplatin the normal cellular DNA repair mechanisms are decreased or inhibited in the presence of a sensitizing agent such as EGF. The cytotoxic effects of the cytotoxic agents are thus potentiated by subsequent administration of a sensitizing agent such as EGF by the inhibitory effect of the EGF on the normal cellular DNA repair mechanism.

BRIEF DESCRIPTION OF THE DRAWINGS

FIG. 1 demonstrates the effect of EGF on sensitivity to the cytotoxic effect of DDP.

FIG. 2C—2008 cells exposed to EGF.

FIG. 4 demonstrates the sensitivity of 2008 cells to DDP in the presence or absence of $10^7$ M TPA for 1 hour.

FIG. 4A—1h drug exposure to DDP concurrently with TPQ; FIG. 4B—24h TPA pretreatment followed by 1h exposure to DDP; FIG. 4C 10 days continuous exposure to DDP with TPA.

FIG. 5 demonstrates the time course of change in DDP sensitivity in the presence or absence of $10^7$ M TPA for 1 hour.

FIG. 6 demonstrates the accumulation of $[^{195m}Pt]DDP$ alone or in the presence of either acetone or TPA: Both 6A and 6B—in 2008 cells.

FIG. 7 demonstrates the effect of phorbol on DDP sensitivity.

FIG. 8 demonstrates the effects of STS on the sensitivity of 2008 cells to TPA.

FIG. 9 demonstrates the TPA effect on the DDP sensitivity of DDP-resistant cells.

DETAILED DESCRIPTION OF THE INVENTION

Two well characterized human ovarian carcinoma cell lines, designated 2008 (Disaia, et al., *Am. J. Obstet Gynecol.* 114: 978 (1972)) and COLO 316 (Woods et al., *Cancer Res.* 39: 4449 (1979)), and a DDP resistant variant 2008/C13*, derived from the parent 2008 cell line (Andrews, et al., *Cancer Res.* 45: 6250 (1985)) were used in these studies. The human cell line 2000 was established from a patient with a serous cystadenocarcinoma of the ovary. The 8-fold DDP resistant cell line 2008/C13* was generated by 13 monthly selections with 1 μM DDP, followed by chronic exposure to stepwise increasing concentrations of DDP, from 0.25 to 5 μM. A resistant subline, designated 2008/C13*5, was obtained by monthly selections with 1 μM DDP. The cells were grown on tissue culture dishes in a humidified incubater at 37° C. and 5% $CO_2$ atmosphere. They were maintained in medium consisting of RPMI 1640 supplemented with 5% heat inactivated fetal calf serum, 2 mM glutamine, 100 Units/ml penicillin, and 100 μq/ml streptomycin (Irvine Scientific, Santa Ana, CA).

Colony forming assays were used to assess the effect of each drug on DDP sensitivity (Andrews, et al., *Chem.-Biol. Interact* 65: 51-58 (1988)). Five ml of suspended cells were plated on 60-mm polystyrene tissue culture dishes (Corning Glass Works, Corning, N.Y.). Cells were allowed to attach overnight, then 10 μl of stock drug solution was added to triplicate plates at each drug concentration. Control plates received diluent alone. After 1 hour, the drug containing medium was aspirated and replaced with drug free medium. Plates were incubated in humidified 5% $CO_2$ air, and after 14 days plates were fixed with methanol and stained with Giemsa Colonies of over 60 cells were counted macroscopically.

Figure 1B:
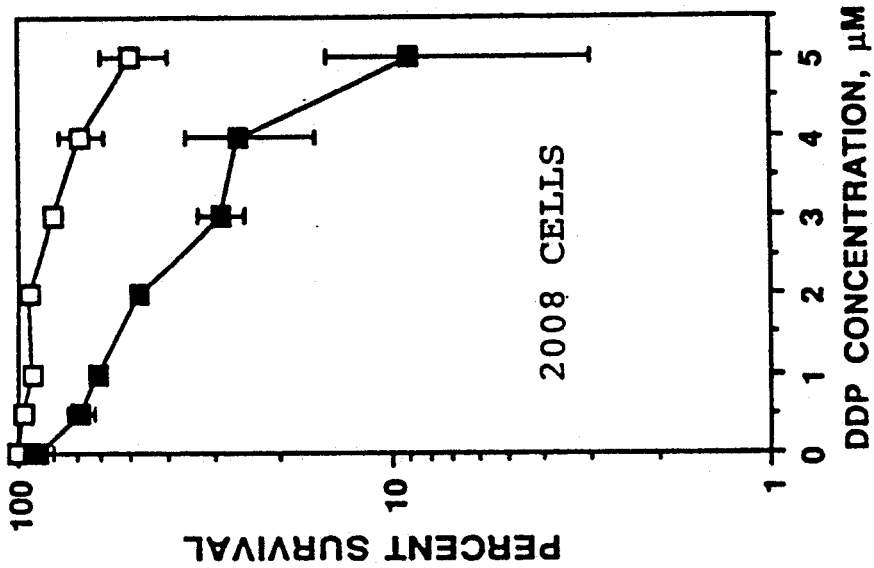
FIG. 1B on 2008 cells.
Figure 1A:
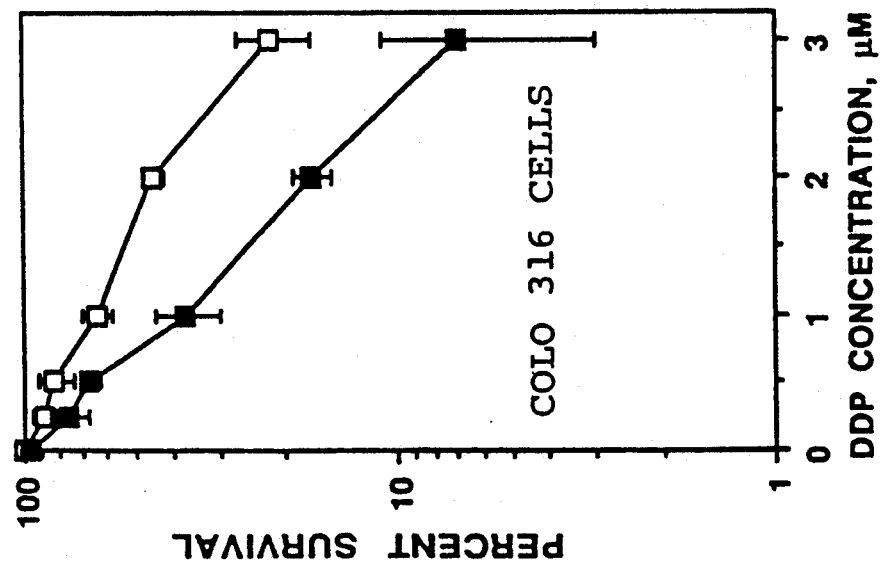
FIG. 1A on COLD 315 cells.

The effect of EGF on the sensitivity of 2008 and COLO 316 cells to DDP is shown in FIG. 1. FIG. 1 demonstrates the effect of EGF on sensitivity to the cytotoxic effect of DDP. 2008 cells and COLO 316 cells were maintained in exponential growth in RPMI Medium 1640 supplemented with 5% heat inactivated bovine calf serum, 2 mM freshly added glutamine, and 1% Fungi bact (Irvine Scientific, Santa Ana, CA). Clonogenic assays were performed by seeding 300 cells per 60 mm plastic dish (Corning Glass Works, Corning, New York, N.Y.). Cells treated with EGF (murine EGF, Sigma Chemical Co, St. Louis, Mo.) were exposed to 10 nM EGF for 1 hr and then to both EGF and DDP during the second hr. The colonies that formed were counted after 10 days of incubation in humidified 5% $CO_2$ at 37° C. Cell clusters containing more than 50 cells were scored as colony. Open squares, DDP alone; closed squares, DDP and EGF. Data points (±SD) are the mean of 3 separate experiments each performed with triplicate cultures.

Cells were expose to 10 nM EGF for 1 hr, and then to both EGF and DDP during a second hr. EGF increased the sensitivity of 2008 cells by 2.9 fold, as quantified by the ratio of the slopes of the dose response curves, and by 3.8 fold, as quantified by the ratio of the $IC_{50}$ values. In the COLO 316 cells increase in sensitivity was 1.7-fold, as quantified by the ratio of the slopes, and 2.0-fold, as quantified by the ratio of the IC50 values. The EGF induced change in slope of the DDP dose response curve was significant for both the 2008 and the COLO 316 cell lines ($P>0.016$, and $P>0.031$, respectively, by two sided t test for the comparison with entreated cells). EGF did not alter DDP cytotoxicity to 2008/C13* cells.

The observed modulation of sensitivity to DDP by EGF was not due to an EGF induced change in growth rate. The effect of both a 2 hr exposure and continuous exposure to 10 nM EGF on growth rate was assayed using the same culture conditions under which EGF enhanced sensitivity to DDP. During the first 5 days after cell seeding, cell growth was exponential. The doubling times of the 2008, 2008/C13*, and COLO 316 cells were 27.9, 28.2, and 29.2 hours, respectively. Neither a 2 hr nor a continuous exposure to 10 nM EGF had any demonstrable impact on the growth rate of these cell lines.

The effect of EGF concentration on the sensitivity of 2008 cells was concentration dependent. A 2 hr exposure to EGF (1 hr before and 1 hr concurrent with DDP) enhanced sensitivity to DDP at EGF concentrations a low as 0.4 nM, and the effect was maximal at concentrations of about 10 nM (approximately 1.5 times the $K_D$ of the EGF receptor). As expected, a further increase in the EGF concentration up to 100 nM produced no additional change in sensitivity t DDP. The EGF-induced increase in sensitivity was not dependent on new protein synthesis. Under circumstances where DDP and EGF together reduced 2008 survival to $31\pm10\%$ of control cells treated with DDP alone, pretreatment with cyclohexamide sufficient to inhibit protein synthesis by 90% produced a survival of $47\pm8\%$.

The time course of the EGF effect on the sensitivity of 2008 cells was determined by exposing cells to 10 nM EGF for 1 hr, and to DDP either concurrently or with an increasing delay between the 1 hr EGF pre-treatment and 1 hr DDP exposure. When given concurrently with DDP, EGF significantly increased sensitivity to DDP reducing survival to $58\pm12\%$ (SD) of that of control cells treated with DDP alone. Sensitivity to DDP increased even further when cells were exposed to EGF for 1 hr prior to treatment with DDP with survival being reduced to $40\pm5\%$ (SD) of control. The EGF mediated increase in sensitivity to DDP persisted for at least 6 hr, but had largely disappeared by 24 hr.

In addition to enhancing sensitivity to DDP, and despite the lack of effect on growth, a 2 hr exposure to EGF had marked effects o the morphology of the 2008 and COLO 316 cells. FIG. 2 demonstrates the morphologic changes induced by EGF. Cells were seeded on 60 mm plastic dishes at a density of 300 cells per dish, allowed to attach overnight and exposed to 10nM EGF for 2 hours on the following day. Colonies were inspected by light microscopy after 10 days of incubation in the absence of EGF. Untreated cells (COLO 316 cells, left upper panel; 2008 cells, right upper panel) showed a dense monolayer of ovoid cells with round nuclei and dense chromatin. The colonies formed by the COLO 316 cells appeared somewhat denser. The lower panels show cells exposed to EGF (COLO 316, left panel; 2008 cells, right panel). In both cell lines EGF induced a marked scattering of the colonies and the formation of prominent dendritic processes.

At the macroscopic level, colonies formed by the 2008 and COLO 316 cells 10 days after a 2 hr exposure to 10 nM EGF were much larger and stained less intensely with Giemsa. At the microscopic level, colonies formed from untreated cells consisted of tightly packed cells, whereas colonies arising after EGF treatment consisted of widely scattered cells of which 10 to 20% had formed prominent dendritic processes. It was of particular interest that 2008/C13* cells, in which EGF failed to alter DDP responsiveness, showed no morphologic response to a 2 hr EGF exposure.

The $K_D$ of the EGF receptor and the receptor number per cell were determined by Scatchard analysis (Scatchard, *Ann.N.Y. Acad. Sci.* 51: 660 (1949)) in the DDP sensitive 2008 and COLO 316 cells, and the DDP resistant 2008/C13* subline. The data is summarized in Table 1.

$^{125}$I EGF bindinq assays were performed with some modifications as described by Kawamoto (Kawamato et al., *Proc. Natl. Acad. Sci. USA* 80: 1337 (1983)). 3-$^{125}$I iodotyrosyl EGF (human recombinant), specific activity 9000 Ci/mmol, was purchased from Amersham Corporation (Arlington Heights, Ill.). Subconfluent 2008, 2008/C13*, and COLO 316 cells grown in 150 x 25 mm plates were fixed with 0.2% paraformaldehyde for 10 minutes at room temperature to prevent receptor internalization during incubation with EGF (Willingham et al., *J. Biol. Chem.* 82: 614 (1979)). Cells were scraped off with a rubber policeman and washed 3 times with PBS (phosphate buffered saline) containing 0.2% bovine serum albumin (PBS/albumin) and resuspended in the same buffer at a cell density of $5\times10^6$ per ml. For binding assays, 200 µl of cell suspension (approximately $1\times10^6$ cells) were incubated with 1 uCi dissolved in 200 µl PBS/albumin. After a 2 hr incubation, cells were quantitatively collected on low protein binding hydrophilic Durapore membranes (pore size 0.22 µm, purchased from Millipore Corporation, Bedford, Mass.) by suction. To prevent nonspecific binding of EGF, the filters were prewet with PBS/albumin. After cell collection, the filters were washed 5 times with PBS/albumin. The filters were dried and radioactivity was measured in a gamma counter. Calculation of receptor number and $K_D$ was performed as described by Scatchard. Mean and standard deviation of 3 different experiments are shown.

TABLE 1

Scatchard Analysis of EGF Binding.

| Cell Line | Fold increases in resistance To DDP | Number of EGF Receptors Per Cell ($\times 10^4$) | Dissociation Constant ($K_D$, nM) |
|---|---|---|---|
| 2008 | 1 | 16.5 ± 0.7 | 2.4 ± 1.3 |
| 2008/C13 | 8 | 5.8 ± 0.9[1] | 4.0 ± 0.3 |
| COLO 316 | 1 | 4.3 ± 0.4 | 4.0 ± 1.4 |

[1] $P > 0.0007$ by two-sided t-test for the comparison with 2008 cells.

The Scatchard plots were monophasic in all cell lines examined, suggesting the presence of a single class of EGF receptors, with the same $K_D$. The $K_D$ and EGF receptor number per cell for 2008 and 2008/C13* cells were of the same order of magnitude. Thus, neither the absolute receptor number nor the $K_D$ predicted the ability of EGF to modulate DDP responsiveness, whereas resistance to DDP rendered the cells refractory to EGF enhancement of DDP sensitivity and EGF induced changes in cell morphology.

The functionality of the EGF receptors was assayed in 2008 cells and 2008/C13* cells by demonstrating down-regulation of the receptor number upon binding to EGF. The receptor number was determined by staining with mAB 455, specific for the human EGF receptor, which does not competitively inhibit the binding of EGF to it receptor (Sato, et al., *Mol. Biol. Med.* 1: 511 (1983); Kawamoto, et al., *Anal. Biochem.* 130: 445 (1983)). A 1 hr incubation of 2008 and 2008/C13* cells with 100 nM EGF at 37° C. caused down regulation of 60-70% of the EGF receptors on both types of cells as compared with control cells treated with 100 nM EGF for 1 hr on ice (a condition known to prevent receptor down-regulation). Usinq EGF receptor mutants lacking intrinsic protein tyrosine kinase activity, it has been convincingly shown that tyrosine kinase activity is essential for signal transduction and for receptor down regulation upon binding to EGF (Honegger et al., *Cell* 51: 199 (1987); Honegger et al., *Mol. Cell Biol.* 7 (12):4568, (1987)). Therefore, it can be concluded that both the 2008 and 2008/C13* cells have functional EGF receptors.

Figure 3:
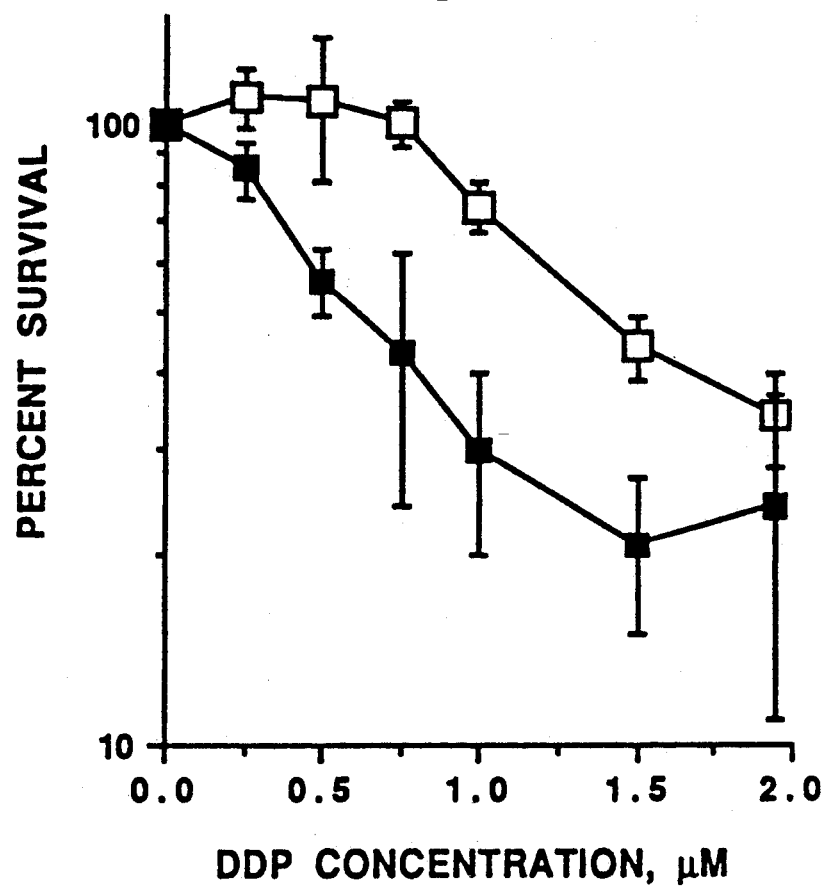
FIG. 3 demonstrates the effect of EGF receptor number on cell response to DDP.

To demonstrate that the modulatinq effect of EGF on sensitivity to DDP was transduced by the EGF receptor, the effect of EGF on the DDP sensitivity of mouse fibroblast C127 cells stably transfected with a plasmid construct containing the human EGF receptor gene under the control of the transferrin receptor 3'inducible regulator (McClelland, et al., *Cell* 39: 267 (1984)) was examined. Expression of the transferrin receptor gene is normally under the control of the transferrin 3'inducible regulator, and is regulated by iron (Owen and Kuhn, *EMBO J.* 6: 1287 (1987)). Incubation with the iron chelator desferrioxamine induces expression of the transferrin receptor gene (Bridqes and Cudkowicz, *J.Biol. Chem.* 259: 12970 (1984)). Expression of the human EGF receptor in transfected cells was visualized by staining with the monoclonal antibody 528 specific for the human EGF receptor (Sato, et al., *Mol. Biol. Med.* 1: 511 (1983); Kawamoto, et al., *Anal. Biochem.* 130: 445 (1983)). Desferrioxamine 10nM increased the number of human EGF receptors by approximately 2 -fold. Since C127 cells do not form uniform colonies, the sensitivity of control and desferrioxamine-induced cells to DDP was compared by using a growth rate assay in which the cell number was quantified by tetrazolium dye reduction (Scudiero et al., *Cancer Res.* 48: 4827 (1988)). Desferrioxamine at a concentration of 10 uM was nontoxic to transfected C127 mouse fibroblasts even after prolonqed incubation for 2 weeks, and did not modulate the sensitivity of transfected C127 cells in the absence of EGF. FIG. 3 demonstrates the effect of EGF receptor number on cell response to DDP. Closed squares, transfected C127 mouse fibroblasts pretreated with desferrioxamine; open squares, untreated cells. C127 mouse fibroblasts were transfected with the human EGF receptor gene under control of the transferrin 3'inducible requlator. One aliquot of cells was incubated in 10 uM desferrioxamine for 60 hrs which induced EGF receptor expression approximately 2-fold, while another was cultured under identical conditions in the absence of desferrioxamine. Using the tetrazolium assay, the effect of DDP on growth rate was determined by seeding 1500 cells in 180 μl of Dulbecco's Modified Eagle Medium (DME) containing 4.5 gm per liter glucose, 10% heat inactivated fetal calf serum, 25 ug/ml human transferrin (holo-form), and 10 nM EGF. DDP at different concentrations was added in 20 μl of saline to triplicate culture wells, and cultures were incubated for 6 days in humidified 5% $CO_2$ in air at 37° C. MTT 3 (4,5 dimethylthiazol 2-yl)-2,5-diphenyl tetrazolium bromide (Siqma, St Louis, Mo.) was prepared at 1 mq/ml in DME media and on day 7, 50 μl were added to the microculture wells. After a 4 hr incubation at 37° C., all the media was removed from each well, and 150 μl of 100% DMSO (dimethyl sulfoxide) was added to solubilize the MTT-formazan product. After thorouqh mixinq, absorbance at 540 nm was measured with a Molecular Devices Vmax Kinetic microplate reader.

FIG. 3 shows that, in the presence of 10 nM EGF, the desferrioxamine treated, transfected C127 cells were approximately 2 fold more sensitive to the cytotoxicity of DDP than control cells. Thus, within a cell line sensitivity to DDP can be requlated by both EGF and EGF receptor number.

These results indicate that sensitivity to DDP can be regulated by both EGF concentration and EFG receptor number, and this provides stronq evidence that the effect was, in fact, mediated via the EGF receptor. The rapid onset of the EGF effect and the fact that it was not blocked by cyclohexamide suggest that the enhanced sensitivity is a direct result of the protein phosphorylation cascade initiated by the EGF receptor. The results also indicate that the ability of EGF to enhance sensitivity is linked with its ability to induce a change in cell morphology. EGF produced both effects in the DDP-sensitive 2008 cells, but neither effect in the DDP-resistant 2008/C13* cells. Thus, the DDP-resistant cells have one or more defects in the EGF signal transduction pathway. The ability of EGF to induce receptor down regulation indicates that the initial steps in the signal transduction pathway, i.e. binding of EGF to its receptor and receptor autophosphorylation, are intact in both the DDP sensitive and resistant cells. One of skill in the art will readily see that the foregoing assays may be utilized to assess the usefulness of other agents related to EGF or its pathway, to practice the present invention.

EGF produces a large number of changes in the cellular physiology of responsive cells, and at this time it is no apparent which of these contribute to the enhanced sensitivity to DDP. It is clear, however, that an EGF mediated change in cell cycle phase distribution and growth rate is not required. The onset of the effect is rapid, and the time course of enhancement parallels the effect of EGF of the induction of c-myc in several other cell systems (Bravo, et al., *EMBO J.* 4: 1193 (1985); (Fernandez Pol, et al., *Biochem. Biophys. Res. Commun.* 144: 1197 (1987)). Recently, exposure of CaSki human squamous carcinoma cells to EGF has been shown to enhance radiosensitivity (Kwock and Sutherland, *J. Natl. Cancer Inst.* 81: 1020 (1989)). It is not known whether there is a single element of the EGF signal tranduction pathway capable of regulatinq both radiosensitivity and sensitivity to DDP, or whether different elements of the EGF signal transduction pathway are independently mediating these two effects.

The observation that EGF can modulate sensitivity to DDP, and can commit two human ovarian carcinoma cell lines to a long-lasting change in morphology consistent with activation of a differentiational program are important for two reasons. First, although the degree of EGF enhancement of DDP sensitivity is in the range of 2 to 4 -fold, this represents a highly clinically significant effect since most patients with acquired DDP resistance have relatively low levels of resistance. Several types of human tumors such as malignant glioma, adrenal carcinoma, hepatoma, ovarian, lung and breast carcinoma are known to express unusually large numbers of EGF receptors in vivo (Libermann et al., Cancer Res. 44: 753 (1984); Xu et al., Proc. Natl. Acad. Sci. USA 81: 7308 (1984); Kamata et al., Cancer Res. 46: 1648 (1986); Meyers et al., J. Cell Biochem. 38: 87 (1988); Bauknecht et al., Gynec. Oncol. 29: 147 ((1988))). Thus, in practicing the present invention, EGF, as well as other sensitizing agents, can be used to selectively enhance the DDP sensitivity of these tumors without increasing the toxicity of DDP to normal tissues at the same time.

The number of EGF receptors can be increased by a variety of agents available for clinical use such as retinoic acid (Thompson and Rosner, J. Biol Chem. 264: 3230 (1989)), estrogen (Mukku and Stancel, J. Biol. Chem. 260: 9820 (1985)), progesterone (Murphy, et al., Biochem. Biophys. Res. Commun. 150: 192 (1987)), triiodothyronine (Fernandez-Pol, J. Biol. Chem. 264: 4151 (1989)), and androgens (Mulderet et al., J. Steroid Biochem. 32: 151 (1989)). Thus, the present invention teaches one to enhance in vivo tumor responsiveness to DDP using one or more of these modulating agents. Secondly, in practicing the present invention, one may use EGF to stimulate differentiation of ovarian carcinomas, thus potentially reducing the degree of malignancy.

Other sensitizing agents are also effective in enhancing the cytotoxicity of DDP. The following Examples illustrate the effectiveness of TPA in enhancing the sensitivity of cancer cells to DDP.

EXAMPLE 1

Effect of TPA on DDP Sensitivity

Figure 4A:
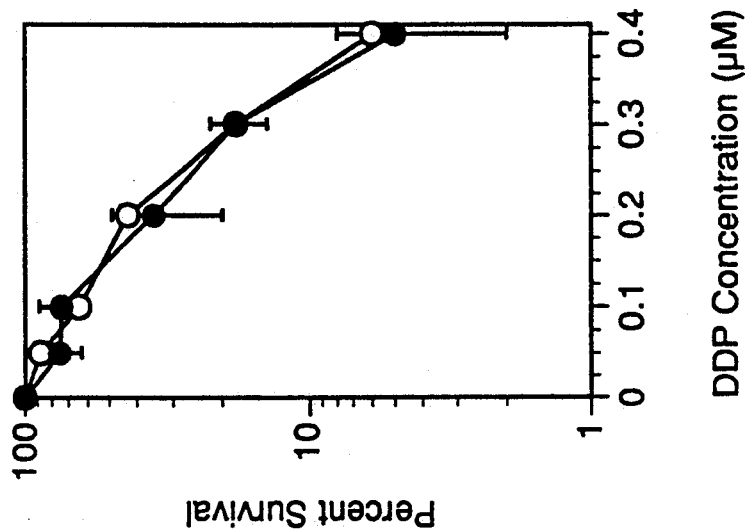
Figure 4B:
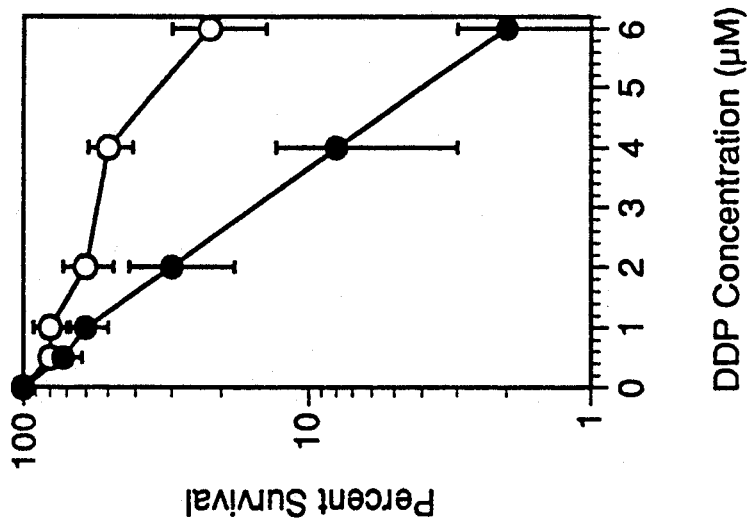
Figure 4C:
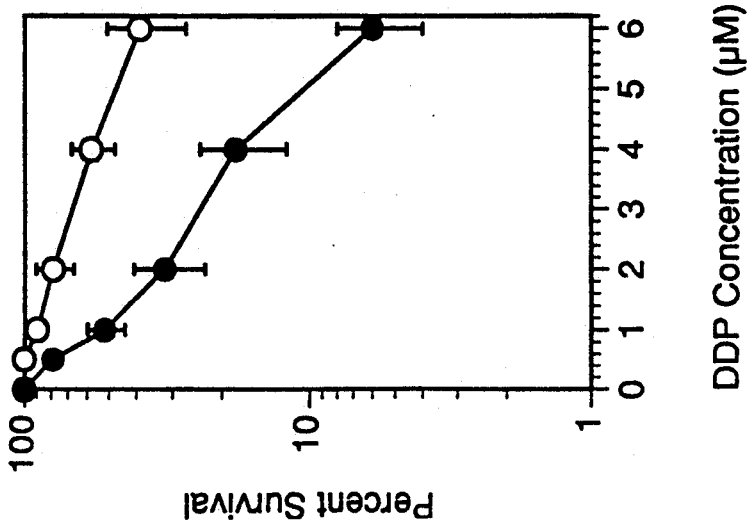

One hr. exposure to TPA or phorbol was performed by adding drugs at the concentration of $10^7$ nM to each plate concomitantly with DDP. Stock solutions consisted of $10^3$ M TPA or phorbol in acetone. In assays involving continuous exposure to DDP with or without TPA, drugs were left in these cultures for the full period of colony formation. FIG. 4 demonstrates the sensitivity of 2008 cells to DDP in the presence ( ) or absence ( ) of $10^7$ M TPA. Cells were treated as follows: Left, 1-h drug exposure to DDP concurrently with TPA; Middle, 24-h TPA pretreatment followed by 1-h exposure to DDP; Right, 10 days continuous exposure to DDP with TPA. Drug cytotoxicity was determined by colonogenic assay. Cultures not containing TPA received an appropriate dilution of acetone as a vehicle control. Points, mean values of three experiments performed with triplicate cultures; bars, S.D.

As demonstrated on FIG. 4, when 2008 cells were exposed concurrently for 1 h to 0.1 μM TPA and DDP, TPA increased DDP sensitivity. The $IC_{50}$ in the absence of TPA was 3.07±0.6 μM (S.D.), whereas in the presence of TPA it was 1.2±0.4 μM (S.D.). Thus, TPA produced a 2.5 fold increase in sensitivity. When cells were treated with a 24-h exposure to 0.1 μM TPA followed by a 1-h exposure to DDP, a similar degree of sensitization was observed. However, when cells were treated with continuous exposure to both the TPA and DDP for the full period of colony formation, no change in DDP sensitivity was evident. TPA at concentrations even up to 1 μM did not cause any toxicity by itself., thus, the interaction between TPA and DDP is truly synergistic as defined by median effect analysis (Chou, and Talalay, Adv. Enzyme Regul. 22: 27-54 (1984)).

EXAMPLE 2

Time Course of Sensitization

Figure 5:
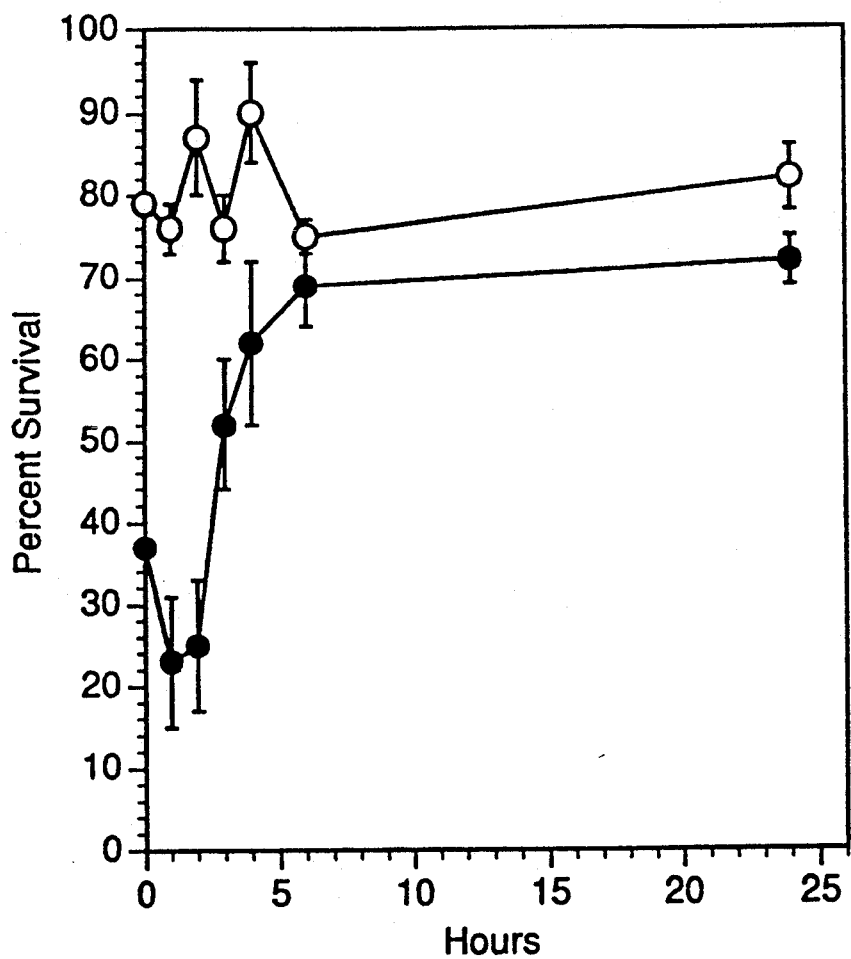

Ovarian carcinoma 2008 cells were exposed to 0N1 μM TPA and 2 μM DDP either concurrently or with increasing time intervals between the start of 1 h TPA and DDP exposures. FIG. 5 demonstrates the time-course of change in DDP sensitivity in the presence ( ) or absence ( ) of $10^7$ μM TPA for 1 hour. After the appropriate drug-free incubation period, cells were treated with 2 μM DDP concurrently for 1 hr. Drug cytotoxicity was determined by colonogenic assay on plastic dishes. Points, mean values of 3 experiments performed with triplicate cultures; bars, SD. FIG. 5 shows that 2 μM DDP reduced colony survival to approximately 80% in the absence of TPA. TPA sensitization was maximal between 1 and 2 h after the start of TPA exposure, but had largely disappeared by 7 h. This time course is consistent with that for activation and inactivation of protein kinase C in other cell systems (Ferguson and Cheng, Cancer Res. 47: 433-441 (1987)).

EXAMPLE 3

DDP Accumulation

Figure 6:
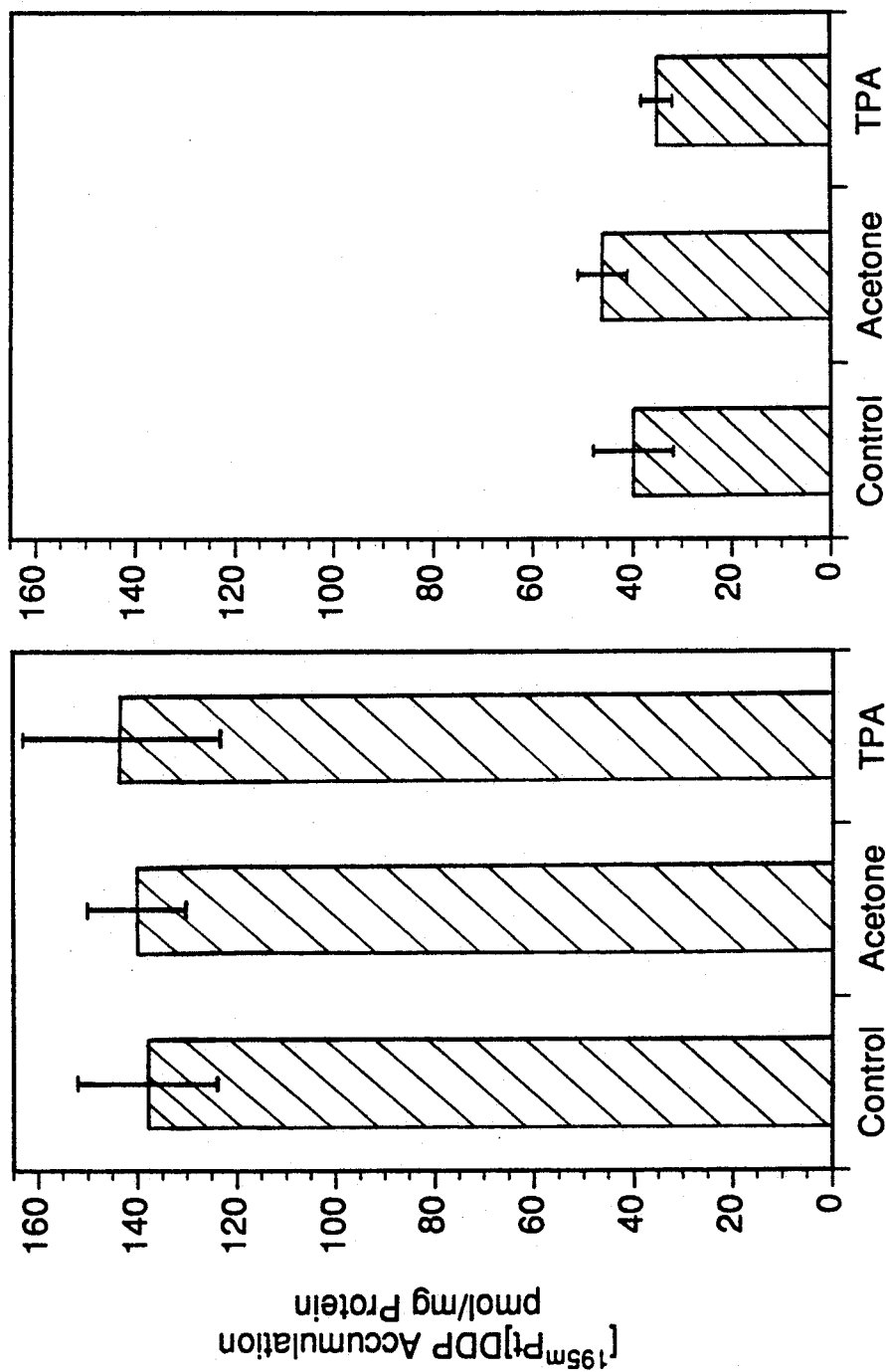

FIG. 6 demonstrates the accumulation of [$^{195m}$Pt]DDP alone or in the presence of either acetone or TPA. Cell associated $^{195m}$Pt was determined by as a measure of DDP accumulation. For DDP accumulation studies, subconfluent monolayers were treated with 37° C. RPMI 1640 medium containing 20 μM[$^{195m}$Pt]DDP. The dishes were immediately returned to the incubater. After 1 hr incubation, the medium was aspirated, the the cells were washed rapidly with 4° C. PBS 4 times. Two ml of 1N NaOH was added and the cells allowed to digest overnight. A forty μl aliquot was used for determination of protein content by the method of Bradford (Bradford, Anal. Biochem. 72: 248-254 (1976)), and the remaining 1.6 ml was counted in glass tubes on a Trak 1191 gamma counter (Tracer Analytic, EIK Grove Village, Ill.). Columns represent the mean values of 3 experiments performed with duplicate cultures. The bars represent the standard deviation.

Example 4

Effect of TPA on Cellular Accumulation of DDP

Cultured 2008 cells were treated concurrently with [195mPt]DDp and TPA for 60 min. A vehicle control consisting of an appropriate dilution of acetone was run concurrently Panel A in FIG. 6 shows that neither the acetone nor the TPA produced any effect on cellular accumulation of [$^{195m}$Pt]DDP. Cells treated with medium alone contained 140±13 pmol/mq of protein, whereas those treated with the acetone control contained 141±7 pmol/mq of protein, and those treated with TPA contained 143±21 pmol/mq of protein. Similar experiments were conducted using either a 10 min TPA preincubation followed by a 1 h concurrent TPA and [195mPt]DDP exposure, or a 24 h preincubation with TPA, and none of them showed any effect on DDP accumulation. Thus, TPA altered sensitivity by a mechanism which does not involve an increased amount of drug entering the cell.

EXAMPLE 5

Determination of cAMP Content

After drug treatment of monolayer cultures in 60 mm dishes, 150 μl of water containing 4 mM EDTA was added to each dish. The cells were scraped, and the samples were stored at −20° C. until assay. The samples were thawed then sonicated for 20 sec at a power setting of 2 (Sonifier 450; Branson, Danbury, CT). A 15 μl aliquot was used for protein assay, and the rest of sample was heated for three min in boiling water bath. After centrifugation the supernatant was used for cAMP assay. Fifty μl of each diluted sample was added to a microtube in duplicate. Fifty μl of the labelled cAMP and 100 μl of the binding protein, purified bovine muscle, were added in each tube in this order. After vortex mixing for 5 sec, the sample in the ice bath was placed into a cold room at 2°–4° C. After 2 hr-incubation, 100 μl of the charcoal suspension was added and the tubes were centrifuged immediately after vortex mixing. A 200 μl aliquot of supernatant was placed in a scintillation vial for counting with a beta counter. The standard curve was constructed using adenosine 3′,5′-cyclic phosphate.

EXAMPLE 6

Effect of TPA on Cellular cAMP Content

The cytotoxicity of DDP can be increased by elevating the cAMP level, indicating that protein kinase A activity is a determinant of DDP sensitivity (Mann, et al., *Proc. Am. Assoc. Cancer Res.* 30: 466 (1989)). To determine whether TPA was enhancing sensitivity via this mechanism, cellular cAMP levels were determined at 10 and 60 min following the start of exposure to 0.1 μM TPA. Forskolin, a potent activator of adenylate cyclase (Seamon, *ISI Atlas Sci. Pharmacol.* 250–253 (1987)), was included as a positive control. The results are shown on Table 2.

TABLE 2

Effect of TPA and Forskolin on cAMP levels

| Treatment | Duration of Treatment | |
|---|---|---|
| | 10 min. mean ± SD[a] | 60 min. mean ± SD[a] |
| No Treatment | 1.9 ± 1.9[b] | 21.4 ± 10.8[b] |
| Acetone | 0.8 ± 1.2[b] | 12.6 ± 6.0[b] |
| TPA | 2.7 ± 1.0[b] | 8.2 ± 2.9[b] |
| Forskolin | 2135.0 ± 305[b] | 6365.0 ± 635[b] |

[a]pmol/mg protein. values are means of 6 experiments.
[b]significantly different from the corresponding value forforskolin at the p > 0.01 level as determined by thet-test on grouped data.

The data presented in Table 2 shows that the acetone vehicle control reduced cAMP content to 59% of the untreated control. TPA reduced the cAMP level to 38% of the untreated control o 65% of the vehicle control at 60 min. In contrast, forskolin increased the cAMP content by 297-fold. Although the biologic significance of the TPA induced reduction in cAMP level is not clear, TPA clearly did not increase cAMP levels into the range associated with forskolin induced enhancement of DDP sensitivity.

EXAMPLE 7

Effect of Phorbol on DDP Sensitivity

Figure 7:
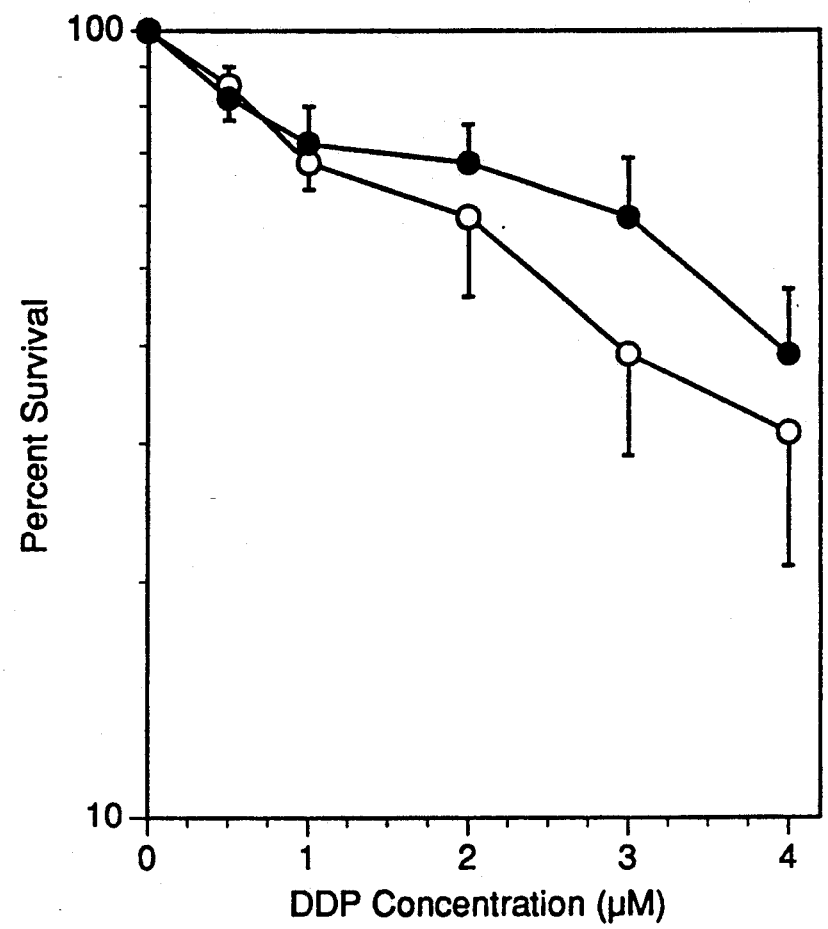

The results presented above suggested that protein kinase C may be involved in regulating DDP sensitivity. To test this further, cells were treated with phorbol, a compound that has structural homology to TPA but not to diacylglycerol, and is known to be inactive as a tumor promoter and activator of protein kinase C. FIG. 7 demonstrates the effect of phorbol on DDP sensitivity. Cells were treated with appropriate concentrations of DDP in the presence ( ) or absence ( ) of $10^7$ M phorbol for 1-h. Drug cytotoxicity was determined by colonogenic assay on plastic dishes. Points, mean values of three experiments performed with triplicate cultures; bars, S.D. As shown in FIG. 7, phorbol failed to enhance DDP sensitivity, and, in fact slightly reduced it.

EXAMPLE 8

Effect of Protein Kinase C Inhibitors on TPA Enhancement of DDP Sensitivity

Staurosporine was used as a potent inhibitor of protein kinase C activity (Tamaki, et al., *Biochem. Biophys. Res. Commun.* 135: 397–402 (1986)). 2008 cells were treated with TPA and DDP either in the presence or absence of 5 nM staurosporine for 1 h. 2008 cells trypsinized from monolayer culture were adjusted to a concentration of 6000 cells per 5 μl in a tissue culture tube (Corning Glass Works, Corning, N.Y.). Five μl of staurosporine (STS) solution was added to each tube to produce a final concentration of 5 nM. Control tubes received water alone. Tubes were preincubated in humidified 5% $CO_2$ in air for 1 hr, followed by another 1 hr incubation with or without 2 μM DDP and/or $10^{-7}$ M TPA. Each tube was then centrifuged and the cells were resuspended in 15 ml of complete medium and used for colony assay. Cloning efficacy under these conditions was 10%.

Figure 8:
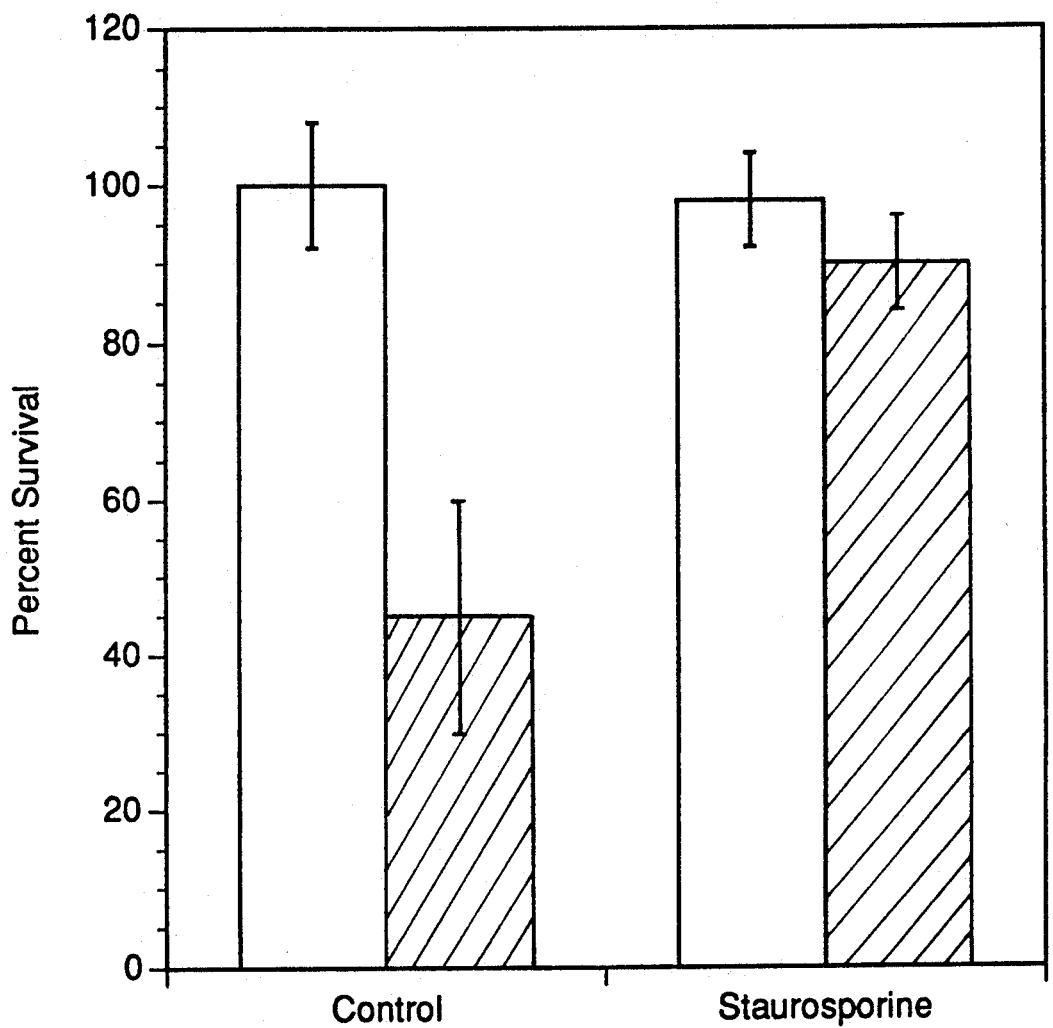

DDP (2μM) alone reduced survival to 85±5% of control, whereas the addition of 0.1 μM TPA enhanced sensitivity, reducing survival to 38±16% of control. FIG. 8 demonstrates the effects of staurosporine on the sensitivity of 2008 cells to TPA. After a 1 h preincubation in medium containing (STS) or lacking (Control) 5 nM STS, cells were treated with 2 μM DDP in the presence (B) or absence (A) of $10^7$ M TPA for 1 h. DDP cytotoxicity was determined by colonogenic assay on plastic dishes. Columns, mean values of three experiments performed with triplicate cultures; bars, S.D. In FIG. 8 these data have been normalized such that the survival with 2 μM DDP alone is 100%, and the addition of TPA reduced survival to 44%. When the cells were pretreated with staurosporine, the effect of TPA was completely blocked, and survival in the presence of all three agents were 96% of that produced by DDP alone. Control experiments showed that staurosporine by itself did not enhance or inhibit sensitivity to DDP. These data strongly suggest that TPA sensitization is mediated by protein kinase C (pkC).

EXAMPLE 9

Enhancement of Sensitivity in DDP resistant Cells

Figure 9:
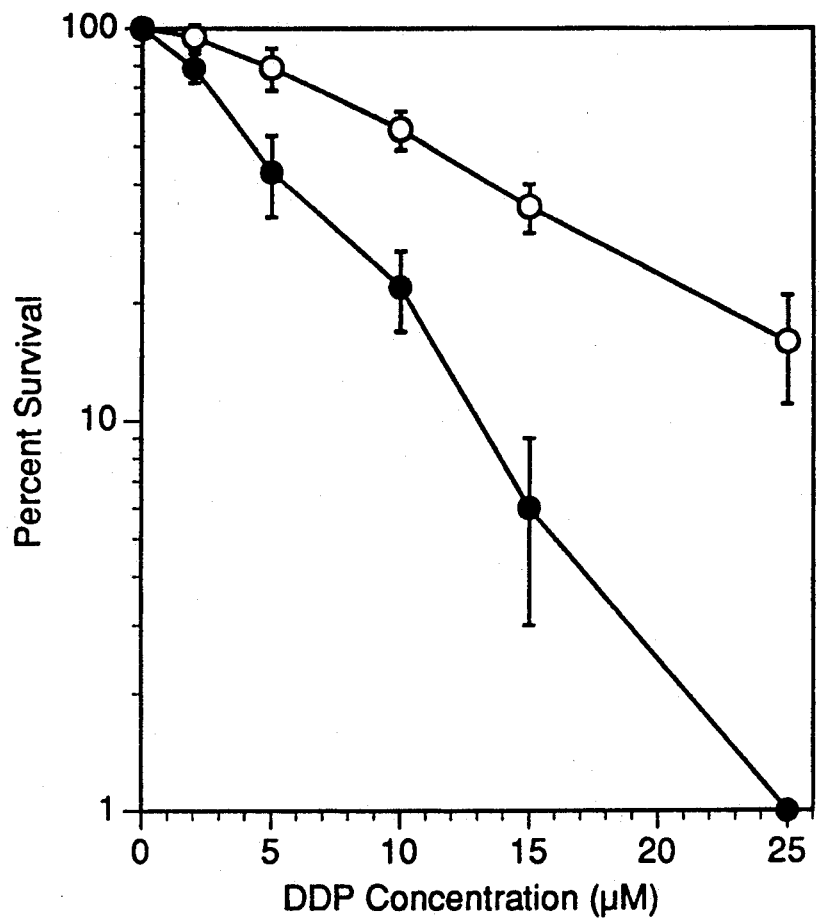

The 2008/C13*5 cell line is 8-10-fold resistant to DDP. FIG. 9 demonstrates the effect of TPA on the DDP sensitivity of DDP resistant cells. C13*5 cells were treated with appropriate concentration of DDP in the presence ( ) or absence ( ) of $10^7$ M TPA for 1 hour. Drug cytotoxicity was determined by by colonogenic assay on plastic dishes. Each point represents the mean values of 3 experiments performed with triplicate cultures. The bars represent the standard deviation.

FIG. 9 shows that when these cells were exposed for 1 h concurrently to TPA and DDP, the IC$_{50}$ was reduced from 13.1±2.7 μM (S.D.) to 4.9±1.4 μM (S.D.). This 2.6-fold sensitization was nearly identical with the 2.5 fold sensitization observed in the DDP-sensitive 2008 cells. At the end of a 1-h incubation, the DDP-resistant 2008/C13*5 cells had accumulated 37.0±3 pmol/mq of protein in cells treated with medium alone, 38.7± to DDP. In order to assess the effect of protein synthesis on the sensitization process, cycloheximide (CHM) was used to inhibit protein synthesis (Wilkinson, and MacLeod, *EMBO J.* 7: 101–109 (1988)). Cells were incubated first with CHM 5 μg/ml for 10 minutes, then with 2 μM DDP alone or with $10^7$ M TPA for 1 hour in serum free medium prior to plating in regular medium for colony formation.

TPA reduced survival to 33 +5% (S.D.) of control in the absence of CHM, and 41±7% (S.D.) of controls in the presence of CHM. Thus, induction of DDP sensitivity was neither blocked nor auqmented by CHM, suggesting that TPA induced changes occured in the absence of protein synthesis.

The data presented herein provide four lines of evidence arguing that protein kinase C is involved in the requlation of DDP sensitivity. First, TPA produced a consistent increase in DDP sensitivity under conditions where, even at a 10 -fold higher concentration, it was totally nontoxic. Although TPA may do other things as well, the major effect by which it mediates changes in cell phenotype appear to be through the activation of protein kinase C. Second, phorbol, an inactive analog of TPA, was unable to enhance DDP sensitivity. Third, the TPA-induced increase in DDP sensitivity was completely blocked by pretreatment of the cells with staurosporine for 1 h. Fourth, the time course of sensitization is consistent with the expected time course for activation or inactivation of protein kinase C following a 1-h TPA exposure. Enhancement was apparent after a 1-h concurrent exposure, was maximal 2 h from the start of TPA exposure, and had disappeared by 7 h. Taken together, these results provide very strong evidence for the involvement of protein kinase C.

Prolonged exposure of cells to TPA produces down regulation of protein kinase C activity in a variety of cell systems, and if it is stimulation of protein kinase C activity that accounts for enhanced DDP sensitivity, one might have expected a 24 h exposure to TPA to reduce sensitivity. Instead, a 24-h exposure to TPA produced exactly the same degree of enhancement as a 1-h exposure. Protein kinase C activity was not measured at the end of the 24-h exposure, and it is possible that the enzyme was not down regulated in these cells as occurs also in KB cells. The protein(s) phosphorlyated by protein kinase C that transmit the signal for enhanced DDP sensitivity is not known. The activation of adenyl cyclase with forskolin, or elevation of cAMP with dibutyl cAMP, enhances sensitivity to DDP in a synergistic manner. Weiner and Scarpa (Wiener and Scarpa, *J. Biol. Chem.* 264: 4324-4326 (1989)) reported that TPA could potentiate the forskolin-induced cAMP response, and Plet et al, (Plet, et al., *Cancer Res.* 48: 3993–3997 (1988)) showed that TPA increased protein kinase C activity. However, several lines of evidence argue against involvement of protein kinase A in the TPA-mediated enhancement of DDP sensitivity. First, direct measurement of cAMP showed no change when cells were treated with TPA. Second, activation of protein kinase A by forskolin is associated with enhanced of DDP uptake into the cell, an effect not produced by TPA. Third, TPA was equally effective in the DDP sensitive 2008 cells and the DDP resistant 2008/C13*5 cells. In contrast, the ability of forskolin to enhance DDP sensitivity is markedly blunted in 2008/C13*5 cells compared to the 2008 cells. These points also argue for the involvement of two separate protein kinases in the regulation of DDP sensitivity.

TPA enhancement of DDP sensitivity was associated with no change in cellular DDP accumulation. Since the cytotoxicity of DDP is believed to be related to the extent of DNA intrastrand, interstrand, and DNA protein cross link formation, the results suggest that intracellular drug is more effective at platinating DNA following TPA treatment. Three mechanisms of DDP resistance have been identified which can participate in this decrease conjugation with glutathione, decreased binding to metallothioneins, or decreased DNA repair. The human metallothionein II gene is one of the TPA inducible genes (Anqel, et al., *Cell* 49: 729–739 (1987); Lee, et al., *Cell* 49: 741–522 (1987)), and, in contrast to what was observed, an increase in the transcription rate of the metallothionein II gene might be expected to result in DDP resistance. TPA miqht down regulate metallothionein in these cells, but the cellular half-life of metallothioneins is long and inconsistent with the time course of TPA induced DDP sensitization. However, one might postulate that TPA is altering the ability of metallothioneins to bind DDP, glutathione levels, glutathione-S-transferase activity, or DNA repair activity. The fact that the TPA effect was equivalent in DDP-sensitive and resistant cells indicates that selection for DDP resistance did not produce any lesions in the TPA signal transduction pathway involved in this sensitization. The signal pathway remains fully intact in both types of cells, indicating that the changes that account for DDP resistance involves biochemical steps distinct from those that participate in the TPA signal transduction pathway.

Administration of the compounds useful in the method of the present invention may be by topical, parenteral, oral, intranasal, intravenous, intramuscular, subcutaneous, or any other suitable means. The dosage administered may be dependent upon the age, weight, kind of concurrent treatment, if any, and nature of the condition being treated. The effective compound useful in the method of the present invention may be employed in such forms as capsules, liquid solutions, suspensions, or elixirs, for oral administration, or sterile liquid forms such as solutions or suspensions. Any inert carrier is preferably used, such as saline, or phosphate-buffered saline, or any such carrier in which the compounds used in the method of the present invention have suitable solubility properties for use in the method of the present invention.

The term "individual" is meant to include any animal, preferably a mammal, and most preferably a cat, doq, cow or human.

One skilled in the art will readily appreciate that the present invention is well adapted to carry out the objects and obtain the ends and advantages mentioned, as well as those inherent therein. The compounds, methods, procedures and techniques described herein are presently representative of the preferred embodiments, are intended to be exemplary and are not intended as limitations on the scope of the present invention. Changes therein and other uses will occur to those skilled in the art which are encompassed within the spirit of the invention and are defined by the scope of the appended claims.

What is claimed is:

1. A method of enhancing the toxicity of cisplatin [(DPO)] in human ovarian carcinoma cells consisting of [administration of a sensitizing agent selected from the group consisting of EGF and TPA to an individual in need of treatment with the cisplatin] administering to individuals in need thereof an effective amount of cisplatin and an effective amount of epidermal growth factor.

* * * * *

UNITED STATES PATENT AND TRADEMARK OFFICE
CERTIFICATE OF CORRECTION

PATENT NO. : 5,252,342
DATED : October 12, 1993
INVENTOR(S) : HOWELL, S.B., et al.

It is certified that error appears in the above-indentified patent and that said Letters Patent is hereby corrected as shown below:

Col. 1, line 21, after "cell lines", insert a --.--.

Col. 1, line 62, italicize "Cancer Res. 37".

Col. 2, line 6, after "into question a", insert the following:

--role for protein kinase C
(Ferguson and Cheng, *Cancer Res.*--.

Col. 2, line 13, correct the spelling of "phosphcrylate" to --phosphorylate--.

Col. 2, line 21, change "312 317" to --312-317--.

Col. 2, line 55, change "steroid like" to --steroid-like--.

Col. 3, line 26, after "phosphoprotein as", insert an --a--.

Col. 3, line 54, change "COLD 315" to --COLO 316--.

Col. 3, line 66, change "TPQ" to --TPA--.

UNITED STATES PATENT AND TRADEMARK OFFICE
CERTIFICATE OF CORRECTION

PATENT NO. : 5,252,342
DATED : October 12, 1993
INVENTOR(S) : HOWELL, S.B., et al.

It is certified that error appears in the above-indentified patent and that said Letters Patent is hereby corrected as shown below:

Col. 4, line 49, after "Giemsa", insert a --.--.

Col. 4, line 58, change "Fungi bact" to --Fungi-bact--.

Col. 5, line 10, change "IC50" to --$IC_{50}$--.

Col. 5, line 11, change "EGF induced" to --EGF-induced--.

Col. 5, line 37, change "sensitivity t" to --sensitivity to--.

Col. 6, line 26, change "3-$^{125}$I" to --3-($^{125}$I--.

Col. 7, line 19, correct the spelling of "Usinq" to --Using--.

Col. 8, lines 7 and 8, change "3 (4,5 dimethylthiazol 2-yl)-2,5-diphenyl" to --3-(4,5 dimethylthiazol 2-yl)-2,5-diphenyl--.

Col. 8, line 9, change "1 mq/ml" to --1 mg/ml--.

UNITED STATES PATENT AND TRADEMARK OFFICE
CERTIFICATE OF CORRECTION

PATENT NO. : 5,252,342
DATED : October 12, 1993
INVENTOR(S) : HOWELL, S.B., et al.

It is certified that error appears in the above-indentified patent and that said Letters Patent is hereby corrected as shown below:

Col. 8, line 14, correct the spelling of "thorouqh" to --through--.

Col. 8, line 21, correct the spelling of "requlated" to --regulated--.

Col. 8, line 25, correct the spelling of "stronq" to --strong--.

Col. 8, line 61, correct the spelling of "regulatinq" to --regulating--.

Col. 9, line 1, correct the spelling of "althouqh" to --although--.

Col. 9, line 48, change "presence ( )" to --presence (●)--.

Col. 9, lines 48 and 49, change "or absence ( )" to --or absence (O)--.

Col. 10, line 1, change "itself.," to --itself;--.

Col. 10, line 14, change "presence ( )" to --presence (●)--.

UNITED STATES PATENT AND TRADEMARK OFFICE
CERTIFICATE OF CORRECTION

PATENT NO. : 5,252,342

DATED : October 12, 1993

INVENTOR(S) : HOWELL, S.B., et al.

It is certified that error appears in the above-indentified patent and that said Letters Patent is hereby corrected as shown below:

Col. 10, line 15, change "or absence ( )" to --or absence (O)--.

Col. 10, line 38, change "$\mu M[^{195m}Pt]DDP$" to --$\mu M[^{195m}Pt]$-DDP--.

Col. 10, line 57, after "concurrently", insert a --,--.

Col. 11, line 57, change "control o 65%" to --control or 65%--.

Col. 12, line 7, change "presence ( ) or absence ( )" to --presence (●) or absence (O)--.

Col. 12, line 64, change "presence ( ) or absence ( )" to --presence (●) or absence (O)--.

Col. 14, lines 21 and 22, after "Lee, et", delete rest of line and insert line 22 beginning with --al., *Cell*--.

UNITED STATES PATENT AND TRADEMARK OFFICE
CERTIFICATE OF CORRECTION

PATENT NO. : 5,252,342
DATED : October 12, 1993
INVENTOR(S) : HOWELL, S.B., et al.

It is certified that error appears in the above-indentified patent and that said Letters Patent is hereby corrected as shown below:

Col. 14, line 25, correct the spelling of "miqht" to --might--.

Col. 14, line 58, correct the spelling of "doq," to --dog,--.

Claim 1, Col. 15, line 6, delete "[(DPO)].

Claim 1, Col. 15, line 7 and Col. 16, lines 1 and 2, delete "[administration of a sensitizing agent selected from the group consisting of EGF and TPA to an individual in need of treatment with the cisplatin]".

Signed and Sealed this

Thirteenth Day of September, 1994

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,252,342
DATED : October 12, 1993
INVENTOR(S) : HOWELL, et al.

Figure 2A:
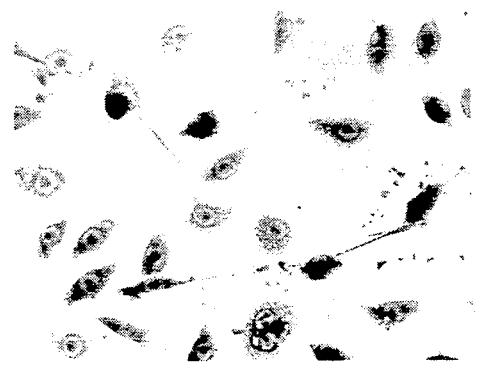
FIG. 2A—untreated COLO 316 cells.
Figure 2B:
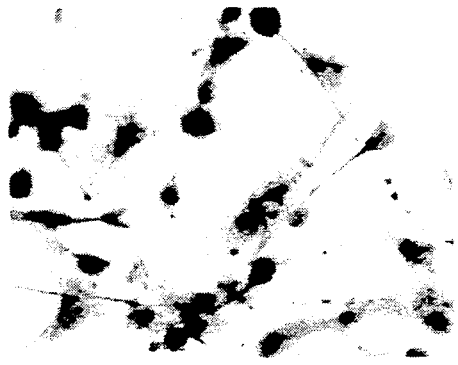
FIG. 2B—untreated 2008 cells.
Figure 2C:
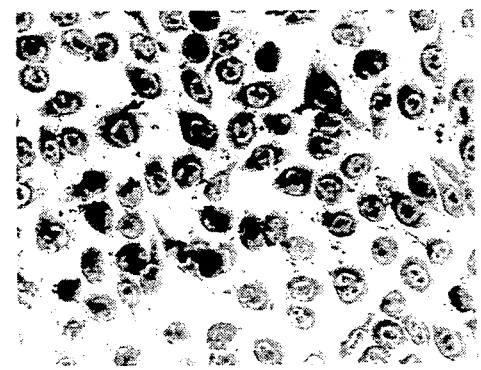
FIG. 2C—COLO 316 cells exposed to EGF.
Figure 2D:
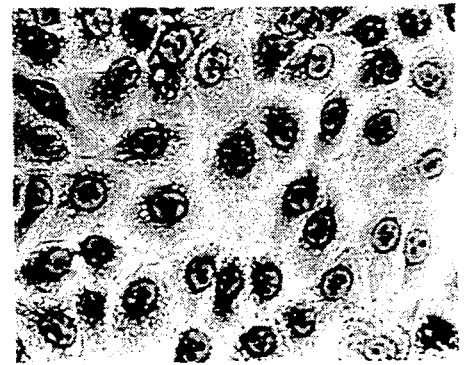
FIG. 2 demonstrates the morphologic changes induced by EGF.

It is certified that error appears in the above-indentified patent and that said Letters Patent is hereby corrected as shown below:

In Figure 2, "FIG. 2A" should read --FIG. 2D--; "FIG. 2B" should read --FIG. 2C--; "FIG. 2C" should read --FIG. 2B--; "FIG. 2D" should read --FIG. 2A--.

In Column 3, line 59, "FIG. 2C" should read --FIG. 2D--.

Signed and Sealed this

Second Day of January, 1996

Attest:

BRUCE LEHMAN

*Attesting Officer*  *Commissioner of Patents and Trademarks*